United States Patent
Whittam

(10) Patent No.: US 9,433,765 B2
(45) Date of Patent: Sep. 6, 2016

(54) SYSTEM AND METHOD FOR PYELOPLASTY INTERNAL-EXTERNAL STENT

(71) Applicant: Benjamin Whittam, Indianapolis, IN (US)

(72) Inventor: Benjamin Whittam, Indianapolis, IN (US)

(73) Assignee: Indiana University Research & Technology Corporation, Indianapolis, IN (US)

( * ) Notice: Subject to any disclaimer, the term of this patent is extended or adjusted under 35 U.S.C. 154(b) by 393 days.

(21) Appl. No.: 14/071,222

(22) Filed: Nov. 4, 2013

(65) Prior Publication Data

US 2014/0128793 A1 May 8, 2014

Related U.S. Application Data

(60) Provisional application No. 61/722,376, filed on Nov. 5, 2012.

(51) Int. Cl.
*A61M 5/00* (2006.01)
*A61M 27/00* (2006.01)

(52) U.S. Cl.
CPC .................................. *A61M 27/008* (2013.01)

(58) Field of Classification Search
CPC ..... A61F 2/042; A61F 202/048; A61M 27/002; A61M 27/008
USPC ............................. 604/8, 9; 623/23.65, 23.66
See application file for complete search history.

(56) References Cited

U.S. PATENT DOCUMENTS

| | | | |
|---|---|---|---|
| 8,512,272 B2 * | 8/2013 | Ostrovsky | A61L 31/128 604/8 |
| 2005/0234388 A1 * | 10/2005 | Amos | A61M 27/008 604/8 |
| 2013/0297039 A1 * | 11/2013 | Lloyd | A61F 2/042 623/23.66 |

* cited by examiner

*Primary Examiner* — Philip R Wiest
(74) *Attorney, Agent, or Firm* — Quarles & Brady, LLP

(57) ABSTRACT

A system and method is provided for the deployment of a ureter between a kidney and a bladder. A stent includes a flexible internal drainage portion, a retention portion, and an external drainage portion. The external drainage portion includes a sharpened tip configured to be passed from through a renal pelvis and out the side of a patient's body from inside the ureter. The stent is arranged to be removable by pulling the external drainage portion and thereby removing the stent out the side of the body.

19 Claims, 2 Drawing Sheets

SYSTEM AND METHOD FOR PYELOPLASTY INTERNAL-EXTERNAL STENT

CROSS REFERENCES TO RELATED APPLICATIONS

This application claims priority to Provisional Patent Application No. 61/722,376 filed on Nov. 5, 2012, the entire contents of which are incorporated herein by reference.

BACKGROUND

The invention is directed to a urinary diversion stent for placement in a ureter. More specifically, the invention is directed to a stent for use in conjunction with laparoscopic or minimally invasive surgery.

Typical urinary diversion stents are designed to be placed either endoscopically or with an open surgical approach. With the advent of laparoscopic and robotic surgery, more reconstructive urologic procedures are being done via a minimally invasive approach. Unfortunately, laparoscopically-deployed, urinary diversion stents suffer from a variety of drawbacks. For example, they can be uncomfortable or irritating to the patient, such as is commonly caused by the use of a retaining mechanism that extends into the bladder. Furthermore, they can be difficult to remove and/or can require additional surgical intervention to address draining interference.

The robotic-assisted pyeloplasty has become a frequently practiced robotic surgery in children. However, there is no stent that meets three important functions: 1. easy laparoscopic/robotic deployment, 2. does not require a secondary procedure to remove, and 3. allows for trial and testing of the repair prior to removal. Typical ureteral stents cause bladder irritation and require either a secondary procedure for removal (and anesthetic for the pediatric population) or an external string hanging from genitalia for patient removal. Typical stents also lack any modality to test or study any anastomosis. Other internal/external stents (e.g., Salle Stent or KISS) are designed to be placed with an open technique, and laparoscopic deployment is unsatisfactory. Further, the KISS lacks a self-retaining device and the Salle Stent has an internal coil that is prone to dislodgment.

Therefore, it would be advantageous to have a system and method for performing robotic-assisted pyeloplasty and associated procedures that does not suffer from the disadvantages of employing traditional urinary diversion stents, particularly when performing pediatric robotic-assisted pyeloplasty.

BRIEF SUMMARY OF THE INVENTION

The present invention overcomes the aforementioned drawbacks by providing a system and method for the deployment of a ureter between a kidney and a bladder. A stent includes a flexible internal drainage portion, a retention portion, and an external drainage portion. The external drainage portion includes a sharpened tip configured to be passed from through a renal pelvis or parenchyma and out the side of a patient's body from inside the ureter. The stent is arranged to be removable by pulling the external drainage portion and thereby removing the stent out the side of the body.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The invention will be better understood and features, aspects and advantages other than those set forth above will become apparent when consideration is given to the following detailed description thereof. Such detailed description makes reference to the following drawings.

Figure 1:
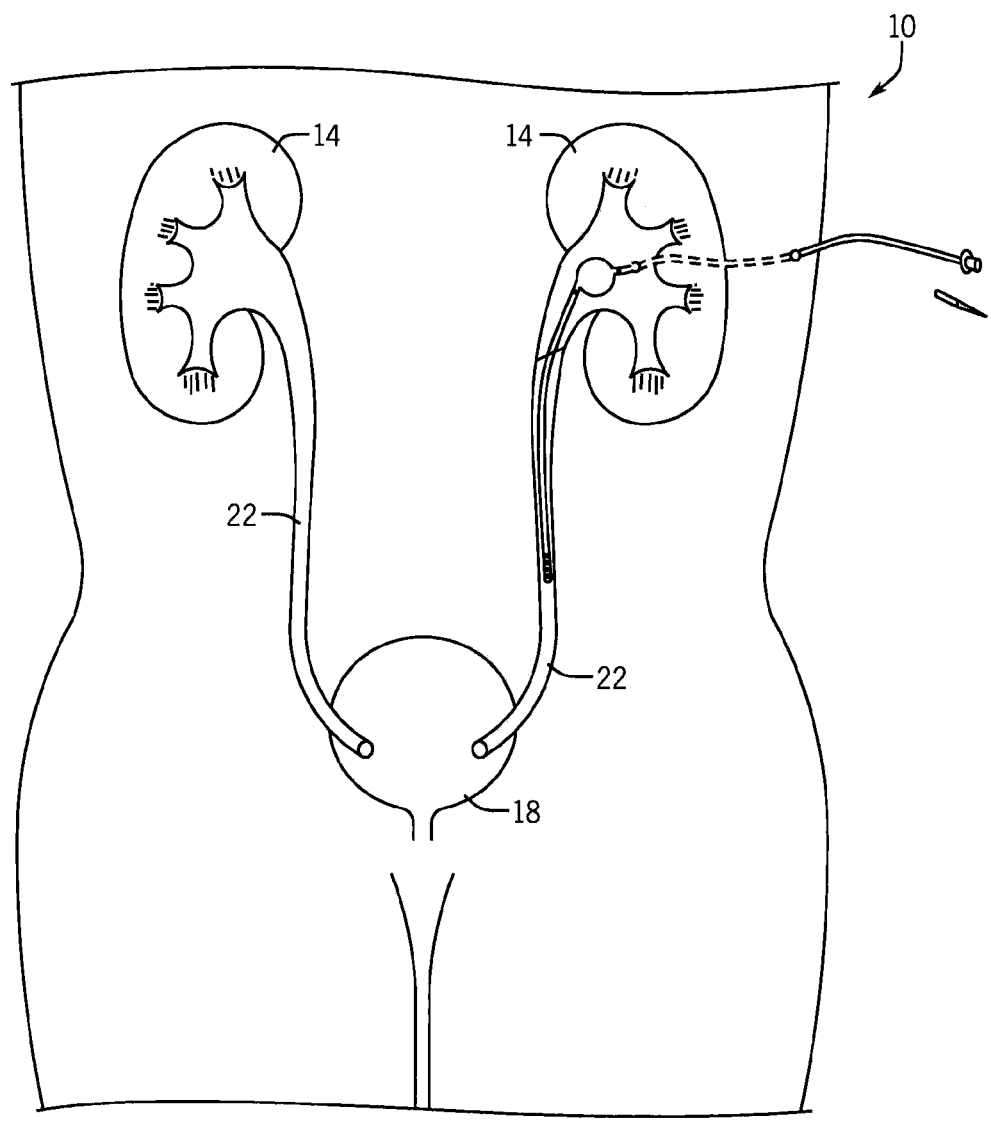
FIG. 1 is a schematic view of the inventive stent implanted in a body.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Figure 2:
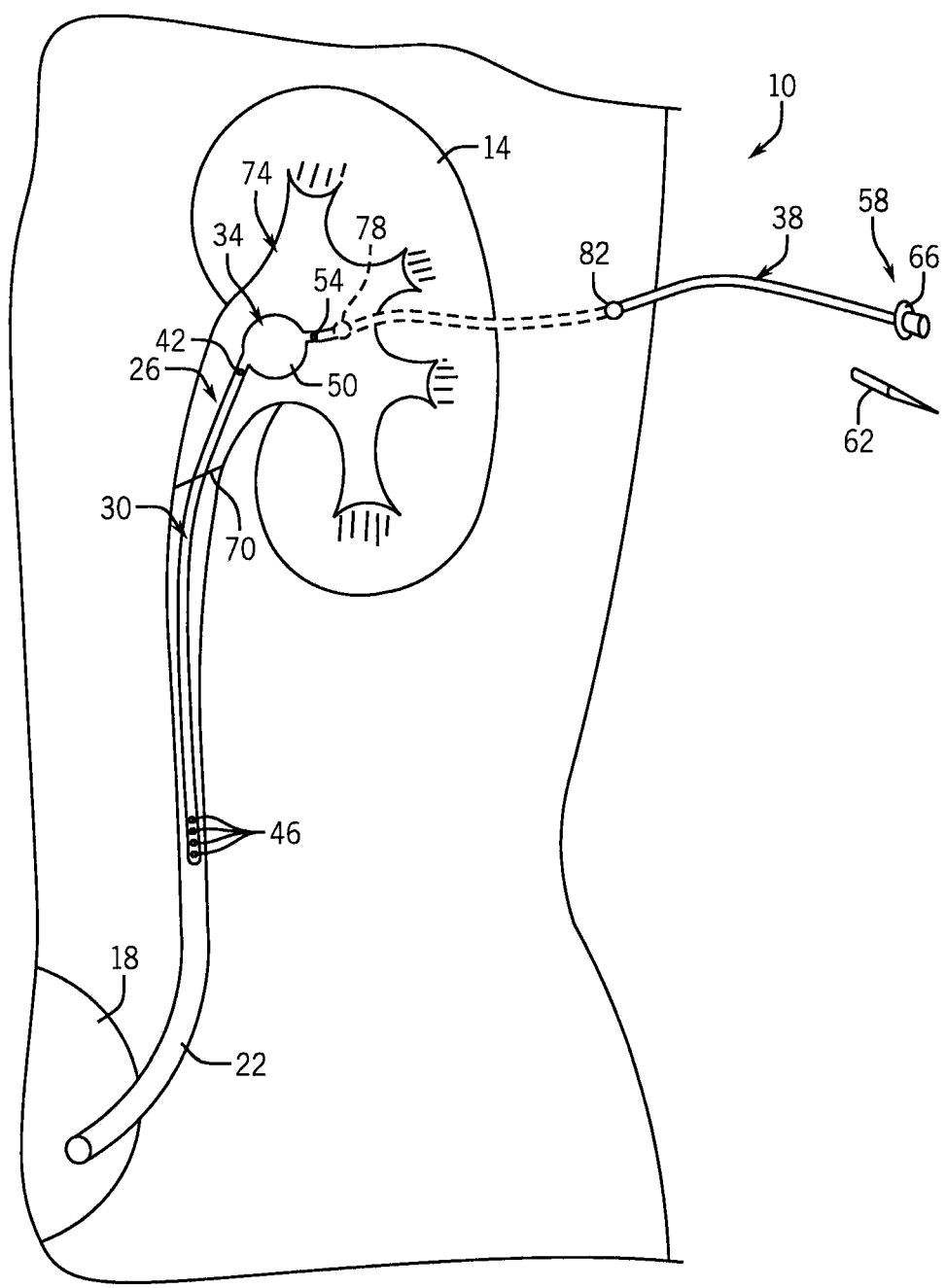
FIG. 2 is a detail view of the stent of FIG. 1.

FIG. 1 shows a subject 10, two kidneys 14, a bladder 18, and two ureters 22 each joining one of the kidneys 14 to the bladder 18. Turning to FIG. 2, a stent 26 is positioned within the subject 10. The illustrated stent 26 is a pyeloplasty internal external stent.

The stent 26 includes an internal drainage portion 30, a retention portion 34, and an external drainage portion 38. The internal drainage portion 30 may be produced of a softer or more malleable material than is typically used for ureter stents and may provide a tapered passageway between an internal collection port 42 and internal drainage ports 46. The illustrated internal collection port 42 and drainage ports 46 are illustrated as apertures. In other constructions, the ports 42, 46 could have other shapes, screens filters, perforations, or design features, as desired, to provide fluid passage therebetween. Additionally, the internal drainage portion may define a constant diameter.

The illustrated retention portion 34 shown as including a selectively inflatable balloon 50. The balloon 50 may be actuated between an inflated state (as shown) and a deflated state (not shown). Actuation may be realized via the external drainage portion 38. In other constructions, the retention portion 34 may include a malencot, pig tail, coil, or other retention device, as desired.

The external drainage portion 38 provides a passageway between an external collection port 54 and an end portion 58. The external drainage portion 38 may define a constant diameter. The end portion 58 is connectable to one of multiple interchangeable ends. The first illustrated end is a needle or point 62 with a sharp tip. The second illustrated end is a valve 66 moveable between an open position and a closed position. Both the point 62 and the valve 66 are selectively secured to the end portion 58 of the external drainage portion 38.

In one construction of the stent 26, the internal drainage portion is made from a separate material that is softer that the retention portion 34 and the external drainage portion 38. In still other embodiments, the entire stent 26 is produced from a single malleable material. The softer, more flexible material is more comfortable for the patient.

In operation, an anastomosis incision 70 is made in the patients ureter 22. The stent 26 is placed into the kidney 14 and ureter 22 through the anastomosis incision 70 with the point 62 attached to the end portion 58. The internal drainage portion 30 is arranged in the mid-ureter 22 without extending into the bladder 22.

The sharpened tip of the point 62 may be pushed through a renal pelvis/parenchyma 74 from the inside thereby forming an internal aperture 78 through which the external drainage portion 38 passes. The point 62 is then pushed further through the body 10 until it emerges, forming an external aperture 82 through which the end portion 58 extends. The point 62 is shaped such that minimal damage is inflicted on the body 10. The point 62 is then removed and the valve 66 is attached to the end portion 58 in the closed position.

With the stent 26 in position, the balloon 50 may be actuated to the inflated position such that the stent is maintained in the desired position. Urine may then drain internally from the kidney 14, through the internal drainage portion 30, and to the bladder 18. The external drainage portion 38 may be used for testing.

When the stent 26 is not longer needed, the balloon 50 is actuated to the deflated position, and the stent 26 is pulled via the end portion 58 through the internal aperture 78 and the external aperture 82 and removed from the body 10.

Therefore, a pyeloplasty internal/external stent is provided that is designed to be deployed laparoscopically. It is compressible and can pass through small (5 mm or less) trocars, as well as through a point of renal pelvis reconstruction. This stent includes a rigid, sharpened end that is designed to pierce either the renal pelvis or renal parenchyma and the body wall without causing significant bleeding or tissue damage. The pyeloplasty internal/external stent can be held in place by a small, inflatable balloon (1-2 cc) or pig-tail device that can be either deflated or straightened to facilitate removal. The intrarenal portion of the stent includes side holes to facilitate drainage both internally and externally. The external drainage portion of the stent can be a rigid or semi-rigid tube that tapers internally to a soft, hydrophilic portion that is designed to be placed in the mid ureter and can be cut to appropriate length. The pyeloplasty internal/external stent provides both internal and external drainage and has the capacity to be capped to provide both an actual test of the anastomosis, as well as an ability to inject the pyeloplasty internal/external stent with contrast to confirm a water-tight anastomosis.

Thus, a pyeloplasty internal/external stent is provided that is easy to deploy laparoscopically given its sharpened external portion that can be passed through the renal pelvis/parenchyma from inside the renal pelvis. The small balloon, malencot, or pig tail keeps the stent in proper position and also allows simple removal. The soft distal end, will reside in mid ureter thus preventing bladder irritation seen with internal dj stents. No secondary procedure would be required to remove this stent in either children or adults.

The pyeloplasty internal/external stent is designed for laparoscopic deployment, but could be used for open procedures as well. The advantages include the ability to study anastomosis, no need for secondary procedure for removal, and no bladder irritation from a distal coil positioned in the bladder. The pyeloplasty internal/external stent can be constructed out of ureteral catheter/stent material with hydrophilic coating on distal ureteral end.

In one embodiment, the invention provides a stent for deployment in a ureter between a kidney and a bladder. The stent includes a flexible internal drainage portion, a retention portion, and an external drainage portion. The external drainage portion includes a sharpened tip configured to be passed from through a renal pelvis and out the side of a patient's body from inside the ureter. The stent arranged to be removable by pulling the external drainage portion and thereby removing the stent out the side of the body.

The internal drainage portion may be produced of a softer or more malleable material than the retention portion and the external drainage portion. Alternatively, the entire stent may be produced from the same malleable material.

The stent is arranged such that it is optimally placed via laparoscopic surgery. Alternatively, the stent may be placed by open surgery.

The present invention has been described in terms of one or more preferred embodiments, and it should be appreciated that many equivalents, alternatives, variations, and modifications, aside from those expressly stated, are possible and within the scope of the invention.

I claim:

1. A stent for deployment in a patient's ureter between a kidney and a bladder, the stent comprising:
   a flexible internal drainage portion;
   a retention portion coupled to the flexible internal drainage portion; and
   an external drainage portion coupled to the retention portion and including a sharpened tip configured to be passed through a renal pelvis and out a side of the patient's body from inside the ureter,
   wherein the stent is arranged to be removable by pulling the external drainage portion and thereby removing the stent out the side of the patient's body.

2. The stent of claim 1, wherein the internal drainage portion is produced of a more malleable material than the retention portion and the external drainage portion.

3. The stent of claim 1, wherein the entire stent may be produced from the same malleable material.

4. The stent of claim 1, arranged to be placed via laparoscopic surgery.

5. The stent of claim 1, wherein the sharpened tip is configured to be removed from the external drainage portion after being passed though the side of the patient's body.

6. The stent of claim 1, further comprising a valve arranged to be coupled to the external drainage portion.

7. The stent of claim 1, wherein the flexible internal drainage portion includes a collection port arranged in fluid communication with the kidney, and a drainage port in fluid communication with the bladder.

8. The stent of claim 7, wherein the flexible internal drainage portion does not extend into the bladder.

9. The stent of claim 7, wherein the collection port is arranged on a first side of an anastomosis surgery site, and the drainage port is arranged on a second side of the anastomosis surgery site.

10. The stent of claim 1, wherein external drainage portion includes a collection port arranged in fluid communication with the kidney.

11. A pyeloplasty internal/external stent for deployment in a patient's body, the stent comprising:
    a retention portion arranged to maintain the position of the stent within the patient's body;
    an internal drainage portion coupled to the retention portion and including an internal collection port arranged to collect fluid, and a internal drainage port arranged to discharge the fluid collected by the internal collection port; and an external drainage portion coupled to the retention portion and including an external collection port arranged to collect fluid, wherein at least a portion of the external drainage portion is configured to extend outside the body through a side of the patient's body, and wherein the external drainage portion includes a tip arranged to push from an interior of the patient's body, through body tissue, and out a side of the patient's body.

12. The stent of claim 11, wherein the tip includes a sharpened point arranged to pass through the patient's body tissue with minimal damage.

13. The stent of claim 11, wherein the external drainage portion includes a valve to provide selective flow from the external collection port.

14. The stent of claim 11, wherein the retention portion includes an inflatable balloon.

15. A method of installing a pyeloplasty internal/external stent in a patient's body, the method comprising:

cutting an anastomosis incision in the patient's ureter;

placing the stent into the patient's kidney and the ureter through the anastomosis incision such that an internal drainage portion is arranged in a mid-ureter section without extending into the patient's bladder;

pushing a point of the stent through the patient's renal pelvis/parenchyma from the inside thereby forming an internal aperture through which an external drainage portion passes;

further pushing the point through the patient's body until it emerges, forming an external aperture through which an end portion of the external drainage portion extends;

removing the point from the external drainage portion;

installing a valve on the end portion of the external drainage portion;

with the stent in position, engaging a retention portion of the stent such that the stent is maintained in a desired position;

draining urine internally from the kidney through the internal drainage portion, and to the bladder;

draining urine externally from the kidney through the external drainage portion for testing;

disengaging the retention portion; and removing the stent through the internal aperture and the external aperture.

16. The method of claim 15, wherein engaging the retention portion includes inflating a balloon.

17. The method of claim 16, wherein disengaging the retention portion includes deflating the balloon.

18. The method of claim 15, further comprising injecting a contrast through the external drainage portion to confirm a water-tight anastomosis.

19. The method of claim 15, further comprising inhibiting flow through the external drainage portion to test a healing success of the anastomosis.

* * * * *